United States Patent
Festo

(10) Patent No.: US 7,026,360 B1
(45) Date of Patent: Apr. 11, 2006

(54) PHARMACEUTICAL COMPOSITIONS CONTAINING COMPOUNDS WITH ACTIVITY FOR THE ENHANCEMENT OF ABSORPTION OF ACTIVE INGREDIENTS

(75) Inventor: Norberto Festo, Lugano (CH)

(73) Assignee: Inpharma S.A., Lugano (CH)

( * ) Notice: Subject to any disclaimer, the term of this patent is extended or adjusted under 35 U.S.C. 154(b) by 0 days.

(21) Appl. No.: 09/673,411

(22) PCT Filed: Feb. 16, 2000

(86) PCT No.: PCT/IB00/00167

§ 371 (c)(1),
(2), (4) Date: Oct. 17, 2000

(87) PCT Pub. No.: WO00/48636

PCT Pub. Date: Aug. 24, 2000

(30) Foreign Application Priority Data

Feb. 18, 1999 (CH) .................... 0311/99

(51) Int. Cl.
*A61K 31/02* (2006.01)
(52) U.S. Cl. .................................. 514/759
(58) Field of Classification Search ............... 568/600, 568/615, 677, 683, 679; 514/759
See application file for complete search history.

(56) References Cited

U.S. PATENT DOCUMENTS

| 5,304,334 A | 4/1994 | Lahanas et al. |
| 5,376,359 A | 12/1994 | Johnson |
| 5,686,102 A * | 11/1997 | Gross et al. ............. 424/450 |

FOREIGN PATENT DOCUMENTS

| EP | 0 390 206 | 10/1990 |
| EP | 0390206 | * 10/1990 |
| EP | 0 723 775 | 7/1996 |
| JP | 62-42922 | 2/1987 |

OTHER PUBLICATIONS

Corti, P., et al., "Near infrared reflectance spectroscopy in the study of atopy Part 3. Interactions between the skin and fomblins," *ANALYST*, vol. 123, pp. 2313-2317, 1998.

Bonina, F., et al., "Three phase emulations for controlled delivery in the cosmetic field," *Int. J. Cosmetic Sci*, vol. 14, pp. 65-74, 1992.

Lehmler, Hans-Joachim, et al., "Liquid Ventilation—A New Way to Deliver Drugs to Diseased Lungs?," *Chemtech*, vol. 29, No. 10, 7-12, pp. 1-10 (Oct. 1999).

* cited by examiner

*Primary Examiner*—Cecilia J. Tsang
*Assistant Examiner*—Taylor Victor Oh
(74) *Attorney, Agent, or Firm*—Ladas & Parry LLP

(57) ABSTRACT

The new pharmaceutical compositions contain, apart from one or more active ingredient(s), between 0.01 and 60% w/w of the compounds of formula I

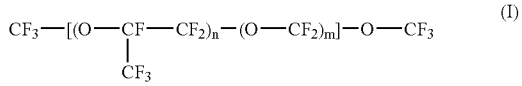

with n and m>18 and <46 and with molecular weights between ~600 and ~8000 for the enhancement of absorption of the active ingredient(s). Moreover, such compositions may contain also between 0.01 and 20% w/w of Phosphatidylcholine.

29 Claims, No Drawings

PHARMACEUTICAL COMPOSITIONS CONTAINING COMPOUNDS WITH ACTIVITY FOR THE ENHANCEMENT OF ABSORPTION OF ACTIVE INGREDIENTS

The invention described herein refers to pharmaceutical compositions, to the use of compounds as agents with activity for the enhancement of absorption of active ingredients and to specific compounds.

The problems related to percutaneous absorption of active ingredients in topical and transdermal pharmaceutical presentations (drug delivery systems) is known and has been the subject matter of patents [1] Peroutaneous absorption: mechanisms-methodology-drug delivery, 2 Ed., Bronaugh Maiibach, MARCEL DEKKER INC.

Among the most significant examples reported In scientific literature it is possible to mention the enhancing activity of decylmethylsulfoxide in increasing percutaneous absorption of idoxuridine [2] Touitou. E. (1988). Int. J. Pharm. 43:1. The effect of dodecylazacycloheptan-2-one (Lauroca-pram, Azone) in enhancing absorption of various molecules was Investigated by Stoughton [3] Stoughton, R. B. (1982), Arch. Dermatol. 118: 474 and by Sugibayashi [4] Sugibayashi, K., Hosoya, K. Morimoto, Y., and Higuchi, W. 1. (1985), J. Pharm. Pharmacol. 37: 578.

Substances made available on the market and initially used in fields other than the pharmaceutical sector, subsequently proved to be of remarkable importance also for the pharmaceutical industry. Among these, we can find the Perfluoropolyether class of compounds (PFPE) [5] obtained by polymerization of hexafluoropropene with oxygen activated by UV radiation and subsequent treatment to obtain a cosmetic product [6] as an excipient for preparations used in the manufacture of products with a barrier effect [7].

SUMMARY OF THE INVENTION

The following invention consists in the use of PFPE to enhance absorption of pharmacologically active ingredients in topical pharmaceutical presentations and/or in transdermal formulations (drug delivery systems) containing mixtures of at least one active ingredient for the enhancement of absorption.

These compounds, if included in pharmaceutical presentations containing an association or at least one active ingredient, can modify the permeating capacity of the active ingredients through the skin, demonstrating a surprising and unexpected capacity to promote the penetration of the active ingredient.

In accordance with the first aspect of the invention, inclusion of a quantity of PFPE may be applied in traditional topical formulations such as, for example, but not limited to: creams, liquid emulsions, ointments, lotions, microemulsions, foams, gels, aspersion powders; and in transdermal formulations (drug delivery systems).

The term PFPE means molecules with a chemical structure

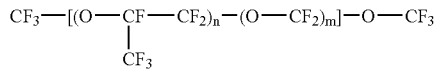

where n/m=20=40
with molecular weights between 650 and 6250, C.A.S. name: 1-Propene, 1,1,2,3,3,3-hexafluoro-, oxidized and polymerized C.A.S. number: 69991-67-9.

Surprisingly, it was found that inclusion of a quantity of PFPE at concentrations between 0.01% w/w and 60% w/w, in topical and/or transdermal (drug delivery systems) formulations, increases the percutaneous absorption of active ingredients by over 5–20 times their normal value, thus enabling improved absorption and optimization of their systemic effects through suitable pharmaceutical presentations.

DETAILED DESCRIPTION OF THE INVENTION

Comprehension of the invention is facilitated by the description of a number of assessments on the percutaneous absorption of certain formulations containing different active ingredients.

Example A illustrates the increase in permeability by approx. 10 times of a formulation containing Troxerutine and 3% PFPE as compared with that of a reference formulation.

Example B demonstrates the correlation between PFPE concentration and percutaneous absorption of formulations containing Nimesulide and increasing concentrations of PFPE.

Example C contains a comparison of the permeation speed of formulations containing non-steroidal antiinflammatory drugs versus formulations to which 3% PFPE has been added.

Example A

Verification of the percutaneous absorption of TROXERUTINE through pig skin using various formulations containing different types of absorption enhancers. In particular, this involved investigation of the release of TROXERUTINE from formulations containing PFPE, Nor-chenodeoxycolic acid and transcutol, versus a reference formulation.

Experimental Section:

Apparatus: Franz Cells (manufacturer: Crown Glass Company Inc., New Jersey)

Franz diffusion cells are one of the main systems used for the investigation of ex-vivo permeation. This study involved the use of three cells each with a 9 mm diameter donor compartment corresponding with a diffusion area of 64 mm².

The receptor compartment has a capacity of 4.8 ml. The receptor chamber is heated to 37° C.± 1.

Test system: HPLC, Gilson, Mod. 305 with Spectra Physics detector, Spectra 200 Mod.

Formulations:

|  | A | B | C | D |
|---|---|---|---|---|
| Troxerutine | 3 | 3 | 3 | 3 |
| Phosphatidylcholine | 7 | 7 | 7 | 7 |
| Tocopherol acetate | 0.5 | 0.5 | 0.5 | 0.5 |
| Sepigel 305 | 4 | 4 | 4 | 4 |
| Methyl-p-hydroxybenzoate | 0.15 | 0.15 | 0.15 | 0.15 |
| Propyl-p-hydroxybenzoate | 0.05 | 0.05 | 0.05 | 0.05 |
| Phenoxyethanol | 1 | 1 | 1 | 1 |
| PFPE | 3 | — | — | — |
| Nor-chenodeoxycolic acid | — | 0.4 | — | — |

-continued

|  | A | B | C | D |
|---|---|---|---|---|
| Transcutol | — | — | 15 | — |
| Purified water q.s. to: | 100 | 100 | 100 | 100 |

Preparation of the Skin

The pig skin samples were taken from the internal ear of pigs that had just been sacrificed.

The samples were soaked in buffer solution at pH 7.4 for 24 hours at 4° C.

The sections of connective tissue and muscle were subsequently removed from the skin and the sample was cut into 2×2 cm squares.

The skin samples were stored at −20° C.

HPLC Operating Test Conditions

| Column: | KP 18, 5 micron Licrospher 100 |
|---|---|
| Mobile phase: | 20% acetonitrile 80% phosphate buffer at pH 6.6 |
| Flow: | 1 ml/min |
| Pressure: | 1.52 Kpsi |
| Wavelength: | 245 nm |
| RT: | 8.51 |

Procedure

The pig skin is placed between the donor compartment and the receptor chamber with the external skin surface facing the upper compartment. The test formulation is placed inside the donor compartment.

The receptor chamber is filled with a phosphate buffer solution at pH 7.4 and at intervals between 0.5 and 8 hours, 2 ml of solution are drawn from this chamber. When each sample is taken fresh buffer solution heated to 37° C. is added in order to replenish the initial volume. The samples are then tested using a HPLC method. Each test is repeated three times.

Results

The results on percutaneous absorption are summarized in the table below

|  | mcg of permeated Troxerutine | | | |
|---|---|---|---|---|
| TIME (h) | A | B | C | D |
| 0.5 | 18.89 | 13.26 | 8.29 | 13.7 |
| 1 | 77.48 | 43.04 | 17.17 | 50.51 |
| 2 | 345.29 | 102.6 | 58.19 | 232.84 |
| 4 | 1,289.11 | 390.80 | 229.46 | 636.68 |
| 6 | 3,999.07 | 614.95 | 530 | 1,053.09 |
| 8 | 12,042 | 1,090 | 714.6 | 1,434.90 |

Conclusions

Formulations B, C, D did not show any difference in absorption, whilst at the eighth hour, formulation A containing PFPE, demonstrated a degree of absorption that was about 9–10 times greater than that of reference formulation D.

Example B

Verification of the absorption of NIMESULIDE through pig skin, using Franz cells, as described in Example A, using various formulations containing different concentrations of PFPE versus a reference formulation.

Formulations:

|  | A | B | C | D |
|---|---|---|---|---|
| Nimesulide | 5 | 5 | 5 | 5 |
| Lactic acid | 2 | 2 | 2 | 2 |
| Ethyl alcohol 95° | 4 | 4 | 4 | 4 |
| Glycerine | 5 | 5 | 5 | 5 |
| PFPE | — | 1.5 | 3 | 4.5 |
| Sepigel 305 | 4 | 4 | 4 | 4 |
| Phosphatidylcholine | 2 | 2 | 2 | 2 |
| Methyl-p-hydroxybenzoate | 0.15 | 0.15 | 0.15 | 0.15 |
| Propyl-p-hydroxybenzoate | 0.05 | 0.05 | 0.05 | 0.05 |
| Purified water q.s. to: | 100% | 100% | 100% | 100% |

Results

The results on permeability are summarized in the following table

|  | mcg of permeated Nimesulide | | | |
|---|---|---|---|---|
| TIME (h) | A | B | C | D |
| 0.5 | 0.15 | 0.16 | 0.59 | 0.83 |
| 1 | 0.27 | 0.39 | 0.59 | 1.21 |
| 2 | 0.35 | 0.72 | 0.97 | 1.70 |
| 4 | 0.86 | 1.14 | 1.24 | 1.91 |
| 6 | 1.15 | 1.54 | 2.21 | 2.38 |
| 8 | 1.54 | 2.24 | 3.21 | 3.73 |
| 24 | 3.53 | 6.00 | 9.71 | 9.86 |

Conclusions

Formulations B, C, D demonstrated an increasing capacity to permeate the skin; this permeating capacity is correlated with the increasing percentage content of PFPE.

Example C

Verification of absorption after 8 hours, of topical formulations containing antiinflammatory drugs versus formulations which also contain 3% PFPE, through pig skin, using Franz cells, as described in Example A.

| Active ingredient | mcg of permeated active ingredient after 8 hours | |
|---|---|---|
| contained in the topical formulation | Base formula | Base formula + 3% PFPE |
| Ketoprofen | 0.64 | 5.33 |
| Diclofenac Sodium | 1.82 | 8.66 |
| Ibuprofen | 0.21 | 6.84 |
| Etodolic Acid | 0.53 | 9.93 |
| Piroxicam | 1.19 | 7.94 |

The invention is characterized by the claims at the end of this description. According to the invention the pharmaceutical compositions contain, apart from one or more active ingredient(s), between 0.01 and 60% w/w of the compounds of formula I

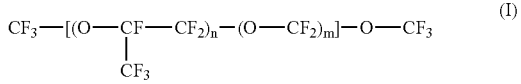

with n and m>18 and <46 and with molecular weights between ~600 and ~8000, as compounds with activity for the enhancement of active ingredient absorption.

Such pharmaceutical compositions may also contain between 0.01 and 20% w/w of Phosphatidylcholine, the compositions preferred are those with 0.1 to 30% w/w of the compounds of formula I with n and m>24 and <36 and with molecular weights between 1000 and 4000 and with 0.1 to 10% w/w of Phosphatidylcholine.

They may also contain other compatible ingredients that are present in the form of creams, emulsions, ointments, lotions, foams, gels and transdermal formulations.

The invention also includes the use of the compounds of formula I

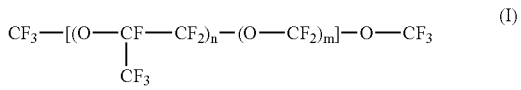

with n and m>18 and <46, preferably >24 and <36, and with molecular weights between ~600 and ~8000, preferably between 1000 and 4000, in pharmaceutical compositions for topical external or internal use for the enhancement of absorption of active ingredients through the derma, cutis, mucosa, rectum, vagina and urethra, with or without Phosphatidylcholine. In particular, such use regards active ingredients that have anabolic, analgesic, androgenic, anesthetic, anorectic, anthelmintic, antiallergic, antiamebic, antiandrogenic, antianginal, antiarrhythmic, antiarteriosclerotic, antiarthritic and antirheumatic, antibacterial, anticholinergic, anticonvulsant, antidepressant, antidiabetic, antidiarrheal, antidiuretic, antiestrogenic, antibiotic, antiglaucoma, antigonatropic, antihistaminic, antihyperlipoproteinemic, antihyperthyroid, antihypertensive, anti-inflammatory, antimalarial, antimigraine, antinauseant, antineoplastic, antiparkinsonian, antiprotozoal, antipruritic, antipsoriatic, antipsychotic, antipyretic, antiseptic, antispasmodic, antithrombotic, antitussive, antiulcer, antiviral, anxiolytic, bronchodilator, CA-blocking or regulating, cardiotonic, stimulating, decongestant, diuretic or enzymatic effect. More specifically, use of this invention regards Troxerutine and Nimesulide and, also 1) α-Adrenergic agonists such as Adrafinil, Adrenoloneu, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline.

2) β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenol, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol.

3) α-Adrenergic blockers such as Amosulalol, Arotinolol, Dapiprazole, Doxazosin, Ergoloid, Mesylates Fenspiride, Indoramin, Labetalol, Nicergoline, Prazosin, Terazosin, Tolazoline, Trimazosin and Yohimbine.

4) β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Bufetolol, Bufuralol, Bunitrolol, Bupranolol, Butidrine, Hydrochloride, Butofilolol, Carazolo, Carteolol Carvedilol, Celiprolol, Cetamolol, Cloranolol, Dilevalol, Epanolol, Esmolol, Indenolol Labetalol, Levobunolol, Mepindolol, Metipranolol, Metoprolol, Moprolol Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol.

5) Alcohol deterrents such as Calcium Cyanamide Citrated, Disulfiram, Nadide and Nitrefazole 6) Aldose reductase inhibitors such as Epalrestat, Ponalrestat, Sorbinil and Tolrestat.

7) Anabolics such as Androisoxazole, Androstenediol, Bolandiol, Bolasterone, Clostebol, Ethylestrenol, Formyldienolone, 4-Hydroxy-19-nortestosterone, Methandriol, Methenolone Methyltrienolone Nandrolone Nandrolone Decanoate, Nandrolone p-Hexyloxyphenylpropionate, Nandrolone Phenpropionate, Norbolethone, Oxymesterone Pizotyline, Quinbolone, Stenbolone and Trenbolone.

8) Analgesics (dental) such as Chlorobutanol, Clove and Eugenol.

9) Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone, Enol Acetate, Dihydromorphine, Dimenoxadol Dimepheptanol, Dimethylthiambutene, Dioxaphetyl Butyrate, Dipipanone Eptazocine Ethoheptazine Ethylmethylthiambutene, Ethylmorphine, Etonitazene, Fentanyl, Hydrocodone, Hydromorphone, Hydroxypethidine) Isomethadone, Ketobemidone, Levorphanol, Lofentanil, Meperidine, Meptazinol, Metazocine, Methadone Hydrochloride, Metopon Morphine, Morphine Derivatives, Myrophine, Nalbuphine, Narceine, Nicomorphine Norlevorphanol, Normethadone, Normorphine, Norpipanone, Opium, Oxycodone, Oxymorphone, Papaveretum, Pentazocine, Phenadoxone, Phenazocine, Phenoperidine, Piminodine Piritramide, Proheptazine, Promedol, Properidine, Propiram, Propoxyphene, Sufentanil and Tilidine.

10) Analgesics (non-narcotic) such as Acetaminophen, Acetaminosalol, Acetanilide, Acetylsalicylsalicylic Acid, Alclofenac, Aminoprofen, Aloxiprin, Aluminum, Bis(acetylsalicylate), Aminochlorthenoxazin, 2-Amino-4-picoline, Aminopropylon, Arminopyrine, Ammonium Salicylate, Antipyrine, Antipyrine, Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum, Acetylsalicylate, Dipyrocetyl, Dipyrone, Emorfazone, Enfenamic, Acid, Epirizole, Etersalate, Ethenzamide, Ethoxazene, Etodolaci, Felbinac, Fenoprofen, Floctafenine, Flufenamic, Acid, Fluoresone, Flupirtine, Fluproquazone, Flurbiprofen, Fosfosal, Gentisic Acid, Glafenine, ibufenac, Imidazole, Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5'Nitro-2'propoxyacetanilide, Parsalmide, Perisoxal, Phenacetin, Phenazopyridine, Hydrochloride, Phenocoll, Phenopyrazone, Phenyl Acetylsalicylate, Phenyl Salicylate, Phenyramidol, Pipebuzone, Piperylone, Prodilidine, Propacetamol Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalate Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac.
11) Androgens such as Boldenone, Fluoxymesterone, Mestanolone Mesterolone, Methandrostenolone, 17-Methyltestosterone, Methaltestosterone, 17α-Methyltestosterone 3-Cyclopentyl Enol Ether, Norethandrolone, Normethandrone, Oxandrolone, Oxymesterone, Oxymetholone, Prasterone, Stanolone, Stanozolol, Testosterone, Testosterone 17-Chloral Hemiacetal, Testosterone 17β-Cypionate, Testosterone Enanthate, Testosterone Nicotinate, Testosterone Phenyl Acetate, Testosterone Propionate and Tiomesterone.
12) Anesthetics (intravenous) such as Acetamidoeugenol, Alfadolone Acetate, Alfaxalone, Ambucaine, Amolanone, Amylocaine, Hydrochloride, Benoxinate, Betoxycaine, Biphenamine, Bupivacaine, Butacaine, Butamben, Butanilicaine, Butethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperodon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine Piridocaine, Polidocanol, Pramoxine, Prilocaine, Procaine, Propanidid, Propanocaine, Proparacaine, Propipocaine, Propofol, Propoxycaine HVdrochlonde, Pseudococaine, Pyrrocaine, Quinine Urea Hydrochloride, Risocaine, Salicyl Alcohol, Tetracaine Hydrochloride, Thialbarbital, Thimylal, Thiobutabarbital, Thiopental Sodium, Tolycaine, Trimecaine and Zolamine.
13) Anorectics such as Aminorex, Amphecloral, Amphetamine, Benzphetamine, Chlorphentermine, Clobenzorex, Cloforex, Clortermine, Cyclexedrine, Dextroamphetamine Sulfates, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfepramone, Methamphetamine, Norpseudoephedrine, Phendimetrazine, Phenmetrazine, Phenpentermine, Phenylpropanolamine Hydrochloride and Picilorex.
14) Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine.
15) Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, Piperazine, piperazine Adipate, Piperazine Citrate, Piperazine Edetate Calcium, Piperazine Tartrate, Pyrantel, Pyrvinium Pamoate, α-Santonin, Stilbazium Iodide, Tetrachloroethylene, Tetramisole, Thiabendazole, Thymol Thymyl N-Isoamylcarbamate, Triclofenol Piperazine and Urea Stibamine.
16) Anthelmintics (Onchocerca) such as Ivermectin and Suramin Sodium.
17) Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziguantel, StibocaPtate, Stibophen and Urea Stibamine.
18) Anthelmintics (Trematodes) such as Anthiolimine and Tetrachloroethylene.
19) Antiacne drugs such as Algestone Acetophenide, Azelaic Acid, Benzoyl Peroxide, Cyoctol, Cyroterone, Motretinide, Resorcinol, Retinoic Acid and Tetroquinone.
20) Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol.
21) Antiamebics such as Arsthinol, Bialamicol, Carbarsone, Cephaeline, Chlorbetamide, Chilorquine, Chlorphenoxamide, Chlortetracycline, Dehydroemetine, Dibromopropamidine, Diloxamide, Diphetarsone, Emetine, Fumagillin, Glaucarubin, Glycobiarsol, 8-Hydroxy-7-iodo-5-quinolinesulfonic Acid, Iodochlorhydroxyquin, Iodoquinol Paromomycin, Phanquinone, Phenarsone Sulfoxylate, Polybenzarsol, Propamidine, Quinfamide Secnidazole, Sulfarside, Teclozan, Tetracycline, Thiocarbamizine, Thiocarbarsone and Tinidazole.
22) Antiandrogens such as Bifluranol, Cyoctol, Cyproterone, Delmadinone Acetate, Flutamide, Nilutamide and Oxendolone.
23) Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil.

24) Antiarrhythmics such as Acebutolol, Acecainide Adenosine, Ajmaline, Alprenolol, Amiodarone, Amoproxan, Aprindine, Arotinolol, Atenolol, Bevantolol, Bretylium, Tosylate, Bucumolol, Bufetolol, Bunaftine, Bunitrolol, Bupranolol Butidrine Hydrochloride, Butobendine, Capobenic Acid, Carazolol, Carteolol, Cifenline, Cloranolol, Disopyramide, Encainide, Esmolol, Flecainide, Gallopamil, Hydroquinidine, Indecainide, Indenolol, Ipratropium Bromide, Lidocaine, Lorajmine, Lorcainide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol Propafenone, Propranolol, Pyrinoline, Quinidine Sulfate, Quinidine, Sotalol, Talinolol, Timolol, Tocainide, Verapamil, Viquidil, and Xibenolol.

25) Antiarteriosclerotics such as Pyridinol Carbamate.

26) Antiarthritic/Antirheumatics such as Allocupreide Sodium, Auranofin, Aurothioglucose, Aurothioglycanide, Azathioprine, Calcium 3-Aurothio-2-propanol-1-sulfonate, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine.

27) Antibacterial (antibiotic) drugs, including:

Aminoglycosides such as Amikacin, Apramycin, Arbekacin, Bambermycins, Butirosin, Dibekacin, Dihydrostreptomycin, Fortimicin(s), Gentamicin, Isepamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin.

β-Lactams including:

Carbapenems such as Imipenem;

Cephalosporins such as Cefaclor Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpiramide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridie, Cephalosporin, Cephalothin, Cephapirin Sodium, Cephradine and Pivcefalexin;

Cephamycins such as Cefbuperazone, Cefmetazole, Cefminox, Cefotetan and Cefoxitin;

Monobactams such as Aztreonam, Carumonam and Tigemonam;

Oxacephems such as Flomoxef and Moxolactam;

Penicillins such as Amidinocillin, Amdinocillin, Pivoxil, Amoxicillin, Ampicillin, Apalcillin, Aspoxicillin, Azidocillin, Azlocillin, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxacillin, Hetacillin, Lenampicillin, Metampicillin, Methicillin Sodium, Mezlocillin, Nafcillin Sodium, Oxacillin, Penamecillin, Penethamate, Hydriodide, Penicillin G Benethamine, Penicillin G Benzathine, Penicillin G Benzhydrylamine, Penicillin G Calcium, Penicillin G-Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin Potassium, Piperacillin, Pivampicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin, Erythromycin Acistrate, Erythromycin Estolate, Erythromycin Glucoheitonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

28) Antibacterial drugs (synthetic), including:

2.4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Niturprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$Formylsulfisomidine, $N^2$-β-D-Glucosylsulfanilamide, Mafenide-4'-(Methylsulfamoyl) sulfanilanilide, p-Nitrosulfathiazole, Noprylsulfamide, Phthalyisulfacetamide, Phthalylsulfathiazole, Salazosulfadimidine, Succinylsulfathiazole, Sulfabenzamide, Sulfacetamide, Sulfachlorpyridazine, Sulfachrysoidine Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N, N'digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol.

29) Anticholinergics such as Adiphenine Hydrochloride, Alverine, Ambutonomium Bromide, Aminopentamide, Amixetrine, Amprotropine, Phosphate, Anisotropine Methylbromide, Apoatropine, Atropine, Atropine N-Oxide, Benactyzine, Benapryzine, Benzetimice, Benzilonium Bromide, Benztropine Mesylate, Bevonium Methyl Sulfate, Biperiden, Butropium Bromide, N-Butylscopolammomium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Dimerine, Dihexyverine, Diphemanil Methylsulfate, N-(1,2-Diphenylethyl)nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, Oxyphencyclimine, Oxyphenonium Bromide, Pentapiperide Penthienate Bromide, Phencarbamide, Phenglutarimide, Pipenzolate Bromide, Piperidolate, Piperilate, Poldine Methysulfate, Pridinol, Prifinium Bromide, Procyclidine Propantheline Bromide, Propenzolate, Propyromazine, Scopolamine, Scopolamine N-Oxide, Stilonium Iodide, Stramonium, Sultroponium Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide.

30) Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone 5-Hydroxytryptophan, Lamotrigine, Magnesium Bromide Magnesium Sulfate, Mephenytoin, Mephobarbital, Metharbital, Methetoin Methsuximide, 5-Methyl-5-(3-phenanthryl)hydantoin, 3-Methyl-5-phenylhydantoin, Narcobarbital, Nimetazepam, Nitrazepam Paramethadione, Phenacemide, Phenetharbital, Phenetu-ride Phenobarbital, Phenobarbital Sodium, Phensuximide, Phenylmethylbarbituric Acid, Phenytoin, Phethenylate Sodium, Potassium Bromide, Primidone, Progabide, Sodium Bromide, Solanum, Strontium Bromide, Suclofenide, Sulthiame, Tetrantoin, Trimethadione, Valproic Acid, Valpromide, Vigabatrin and Zonisamide.

31) Antidepressants, including:
Bicyclics such as Binedaline, Caroxazone, Citatopram, Dimethazan, Indalpine, Fencamine, Indeloxazine Hydrochloride, Nefopam, Nomifensine, Oxitriptan, Oxypertine, Paroxetine, Sertraline, Thiazesim, Trazodone and Zometapine;
Hydrazides/Hydrazines such as Benmoxine, Iproclozide, Iproniazid, Isocarboxazid, Nialamide, Octamoxin and Phenelzine;

Pyrrolidones such as Cotinine, Rolicyprine and Rolipram;
Tetracyclics such as Maprotiline, Metralindole, Mianserin and Oxaprotiline, Tricyclics such as Adinazolam, Amitriptyline, Amitriptylinoxide, Amoxapine, Butriptyline, Clomipramine, Demexiptiline, Desipramine, Dibenzepin, Dimetacrine, Dothiepin, Doxepin, Fluacizine Imipramine, Imipramine N-Oxide Iprindole, Lofepramine, Melitracen, Metapramine, Nortriptyline, Noxiptilin, Opipramol, Pizotyline, Propizepine, Protriptyline, Quinupramine, Tianeptine and Trimipramine; and
others such as Adrafinil, Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

32) Antidiabetics, Including:
Biguanides such as Buformin, Metformin and Phenformin;
Hormones such as Glucagon, Insulin, Insulin Injection, Insulin Zinc Suspension, Isophane Insulin Suspension, Protamine Zinc Insulin Suspension and Zinc Insulin Crystals;
Sulfonylurea derivatives such as Acetohexamide, 1 Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

33) Antidiarrheal drugs such as Acetyltannic Acid, Albumin Tannate, Alkofanone, Aluminum Salicylates-Basic, Catechin, Difenoxin, Diphenoxylate, Lidamidine, Loperamide, Mebiquine, Trillium and Uzarin.

34) Antidiuretics such as Desmopressin, Felypressin, Lypressin, Ornipressin, Oxycinchophen, Pituitary-Posterior, Terlipressin and Vasopressin.

35) Antiestrogens such as Delmadinone Acetate, Ethamoxytriphetol, Tamoxifen and Toremifene.

36) Antifungal drugs (antibiotics), including:
Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and
others such as Azaserine, Griseofulvin, Oligomycins, Neomycin Undecylenate, Pyrrolnitrin, Siccanin, Tubercidin and Viridin.

37) Antifungal drugs (synthetic), including:
Allylamines such as Naftifine and Terbinafine;
Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole Nitrate, Sulconazole and Tioconazole;
Triazoles such as Fluconazole, Itraconazole and Terconazole; and others such as Acrisorcin, Amorolfine, Biphenamine, Bromosalicylchloranilide, Buclosamide, Calcium Propionate, Chlorehenesin, Ciclopirox, Cloxyquin, Coparaffinate, Diamthazole Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Triacetin, Ujothion, Undecylenic Acid and Zinc Propionate.

38) Antiglaucoma drugs such as Acetazolamide, Befunolol, Betaxolol, Bupranolol, Carteolol, Dapiprazole, Dichlorphenamide, Dipivefrin, Epinephrine, Levobunolol, Methazolamide, Metipranolol, Pilocarpine, Pindolol and Timolol.

39) Antigonadotropins such as Danazol, Gestrinone and Paroxypropione.

40) Antigout drugs such as Allopurinol, Carprofen, Colchicine, Probenecid and Sulfinpyrazone.

41) Antihistamines, including: Alkylamine derivatives such as Acrivastine, Bamipine, Brompheniramine, Chlorpheniramine, Dimethindene, Metron S. Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenylpyraline, Doxylamine, Embramine, Medrylamine, Mephenhydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

Piperazines such as Cetirizine, Chlorcyclizine, Cinnarizine, Cilocinizine and Hydroxyzine;

Tricyclics, including:

Phenothiazines such as Ahistan, Etymemazine, Hydroxyzine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole Azelastine Cetoxime, Clemizole, Clobenztropine, Diphenazoline, Diphenhydramine, Mebhydroline, Phenindamine, Terfenadine and Tritoqualine.

42) Antihyperlipoproteinemics, including:

Aryloxalkanoic acid derivatives such as Beclobrate, Bezafibrate, Binifibrate, Ciprofibrate, Clinofibrate, Clofibrate, Clofibric Acid, Etofibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, β-Benzalbutyramide, Carnitine, Chondroitin Sulfate, Clomestrone, Dietaxtran, Dextran Sulfate Sodium, 5,8,11,14,17-Eicosapentaenoic Acid, Eritadenine, Furazabol, Meglutol, Melinamide, Mytatrienediol, Ornithine, γ-Oryzanol, Pantethine, Pentaerythritol Tetraacetate, α-Phenylbutyramide, Pirozadil, Probucol, α-Sitosterol, Sultosilic Acid, Piperazine Salt, Tiadenol, Triparanol and Xenbucin.

43) Antihypertensive drugs, including:

Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Carteolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tertatolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide Meticrane, Metolazone, Paraflutizide, Polythiazide, Tetrachlormethiazide, and Trichlormethiazide;

N-Carboxyalkyl (petide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipine;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidinium Methosulfate, Quinazoline derivatives such as Alfuzosin, Bunazosin, Doxazosin, Prazosin, Terazosin and Trimazosin;

Reserpine derivatives such as Bietaserpine Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, γ-Aminobutyric Acid, Bufeniode, Chlorthalidone, Cicletanine, Ciclosidomine, Cryptenamine Tannates, Fenoldopam, Flosequinan, Indoramin, Ketanserin, Mebutamate, Mecamylamine, Methyldopa, Methyl 4-Pyridyl-Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trinmethaphan, Camsylate, Tyrosinase and Urapidil.

44) Antihyperthyroids such as 2-Amino-4-methylthiazole, 2-Aminothiazole Carbimazole 3,5-Dibromo-L-tyrosine 3,5-Diiodotyrosine, Hinderin, Iodine, Iothiouracil Methimazole Methylthiouracil, Propylthiouracil, Sodium Perchlorate, Thibenzazoline, Thiobarbital and 2-Thiouracil.

45) Antihypotensive drugs such as Amezinium Methyl Sulfate, Angiotensin Amide, Dimetofrine, Dopamine, Etifelmin, Etilefrin, Gepefine, Metaraminol, Midodrine, Norepinephrine, Pholedrine and Synephrine.

46) Antihypothyrold drugs such as Levothyroxine Sodium, Liothyronine, Thyroid, Thyroidin, Thyroxine, Tiratricol and TSH.

47) Anti-Inflammatory (non-steroidal) drugs, including:

Aminoaryicarboxylic acid derivatives such as Enfenamic Acid, Etofenamate, Flufenamic Acid, Isonixin, Meclofenamic Acid, Mefenamic Acid. Niflumic Acid, Talniflumate, Terofenamate and Tolfenamic Acid;

Arylacetic acid derivatives such as Acemetacin) Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizon) Butibufen) Fenbufen and Xenbucin;

Arylcarboxylic acid such as Clidanac Ketorolac and Tinoridine;

Arylpropionic acid derivatives such as Alminoprofen, Benoxaprofen Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid. Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenylbutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine, O-Acetic Acid, Salicylsulfuric Acid, Salsalate and Sulfasalazine;

Thiazinecarboxamides such as Droxicam, Isoxicam, Piroxicam and Tenoxicam; and others such as ε-Acetamidocaproic Acid, S-Adenosylmethionine, 3-Amino-4-hydroxybutyric Acid Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

48) Antimalarial drugs such as Acedapsone, Amodiaquin, Arteether, Artemether, Artemisinin, Artesunate, Bebeerine, Berberine, Chirata, Chlorguanide, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Dibasic.

49) Antimigraine drugs such as Alpiropride, Dihydroergotamine, Ergocornine, Ergocorninine, Ergocryptine, Ergot, Ergotamine, Flumedroxone acetate, Fonazine, Lisuride Methysergid(e), Oxetorone, Pizotyline and Sumatriptan.

50) Antinauseant drugs such as Acetylleucine Monoethanolamine, Alizapride, Benzquinamide, Bietanautine, Bromopride, Buclizine Chlorpromazine, Clebopride, Cyclizine, Dimenhydrinate, Diphenidol, Domperidone, Granisetron, Meclizine, Methallatal, Metoclopramide Metopimazine, Nabilone, Ondansetron, Oxypendyl, Pipamazine, Piprinhydrinate, Prochlorperazine, Scopolamine, Tetrahydrocannabinols, Thiethylperazine, Thioproperazine, and Trimethobenzamide.

51) Antineoplastic drugs in including: Alkylating agents, including:

Alkyl sulfonates such as Busulfan, Improsulfan and Piposulfan;

Aziridines such as Benzodepa, Carboqune, Meturedepa and Uredepa; Ethylenimines and methylmelamines such as Altretamine, Triethylenemelamine, Triethylenephosphoramide, Triethylenethiophosphoramide and Trimethylolmelamine;

Nitrogen mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;

Nitrosoureas such as Carmustine, Chlorozotocin, Fotemustine, Lomustine Nimustine and Ranimustine; and others such as Dacarbazine; Mannomustine, Mitobronitol, Mitolactol and Pipobroman;

Antibiotics such as Aclacinomycins, Actinomycin F1, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin;

Antimetabolites, including:

Folic acid analogs such as Denopterin Methotrexate, Pteropterin and Trimetrexate;

Purine analogs such as Fludarabine, 6-Mercaptopurine, Thiamiprine and Thioguanine; and Pirymidine analogs such as Ancitabine, Azacitidine, 6-Azauridine, Carmofur, Cytarabine, Doxifluridine, Enocitabine, Floxuridine, Fluorouracil and Tegafur;

Enzymes such as L-Asparaginase; and others such as Aceglatone, Amsacrine, Bestrabucil, Bisantrene, Carboplatin, Cisplatin, Defosfamide, Demecolcine, Diaziquone, Eflornithine, Elliptinium Acetate, Etoglucid, Etoposide, Gallium Nitrate, Hydroxyurea, Interferon-α, interferon-β, Interferon-γ, Interleukin-2, Lentinan, Lonidamine, Mitoguazone Mitoxantrone, Mopidamol, Nitracrine Pentostatin, Phenamet, Pirarubicin, Podophyllinic, Acid, 2-Ethylhydrazide, Procarbazine, PSK®, Razoxane, Sizofiran, Spirogermanium, Taxol, Teniposide, Tenuazonic Acid, Triaziquone, 2 2',2"-Trichlorotriethylamine, Urethan, Vinblastine, Vincristine and Vindesine.

52) Antineoplastic (hormonal) drugs, including: Androgens such as Calusterone, Dromostanolone Propionate. Epitiostanol Mepitiostane and Testolactone;

Antiadrenals such as Aminoglutethimide Mitotane and Trilostane; Antiandrogens such as Flutamide and Nilutamide; and Antiestrogens such as Tamoxifen and Toremifene.

53) Antineoplastic adjuncts Including folic acid replenishers such as Folinic Acid.

54) Antiparkinsonian drugs such as Amantadine, Benserazide, Bietanautine, Biperiden, Bromocriptine, Budipine, Carbidopa, Deprenyl, Dexetimide, Diethazine, Droxidopa, Ethopropazine, Ethylbenzhydramine, Levodopa, Naxagolide, Pergolide, Piroheptine, Pridinol, Prodipine, Terguride Tigloidine and Trihexyphenidyl Hydrochloride.

55) Antipheochromocytoma drugs such as Metyrosine. Phenoxybenzamine and Phentolamine.

56) Antipneumocystis drugs such as Eflornithine, Pentamidine and Sulfamethoxazole.

57) Antiprostatic hypetrophy drugs such as Gestonorone Caproate, Mepartricin, Oxendolone and Proscar®.
58) Antiprotozoal drugs (Leshmania) such as Antimony Sodium Gluconate, Ethylstibamine, Hydroxystilbamidine; N-Methylglucamine, Pentamidine, Stilbamidine and Urea Stibamine.
59) Antiprotozoal drugs (Trichomonas) such as Acetarsone, Aminitrozole, Anisomycin, Azanidazole, Forminitrazole, Furazolidone Hachimycin, Lauroguadine, Mepartricin, Metronidazole, Nifuratel, Nifuroxime, Nimorazole, Secnidazole, Silver Picrate, Tenonitrozole and Timidazole.
60) Antiprotozoal drugs (Trypanosma) such as Benznidazole Eflornithine Melarsoprol, Nifurtimox, Oxophenarsine, Hydrochloride, Pentamidine, Propamidine, Puromycin, Quinapyramine, Stilbamidine, Suramin Sodium, Trypan Red and Tryparsamide.
61) Antipuritics such as Camphors, Cyproheptadine, Dichlorisone, Glycine, Halometasone, 3-Hydroxycamphor, Menthol. Mesulphen, Methdilazine, Phenol, Polidocanol, Risocaine, Spirit of Camphor, Thenaldine, Tolpropamine and Trimeprazine.
62) Antipsoriatic drugs such as Acitretin, Ammonium Salicylate, Anthralin, 6-Azauridine, Bergapten(e), Chrysarobin, Etretinate and Pyrogallol.
63) Antipsychotic drugs, including:
Butyrophenones such as Benperidol, Bromperidol, Droperidol, Fluanisone, Haloperidol, Melperone, Moperone, Pipamperone, Spiperone, Timiperone and Trifiuperidol;
Phenothiazines such as Acetophenazine, Butaperazine, Carphenazine, Chlorproethazine, Chlorpromazihe, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;
Thioxanthenes such as Chlorprothixene, Clopenthixol, Flupentixol and Thiothixene;
other tricyclics such as Benzquinamide, Carpipramine, Clocapramine Clomacran, Clothiapine, Clozapine, Opipramol, Prothipendyl, Tetrabenazine and Zotepine; and
others such as Alizapride, Amisulpride, Buramate, Fluspirilene, Molindone, Penfluridol, Pimozide, Spirilene and Sulpiride.
64) Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 5'-Nitro-2'propoxyacetanilide, Propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine.
65) Antirickettsial drugs such as p-Aminobenzoic Acid, Chloramphenicol, Chloramphenicol Palmitate, Chloramphenicol Pantothenate and Tetracycline.
66) Antiseborrheic drugs such as Chloroxine 3-O-Lauroylpyridoxol Diacetate, Piroctone, Pyrithione, Resorcinol, Selenium Sulfides and Tioxolone.
67) Antiseptics, including:
Guanidines such as Alexidine, Ambazone, Chlorhexidine and Picloxydine;
Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Flurosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium;
Mercurial compounds such as Hydraroaphen, Meralein Sodium, Merbromin, Mercuric Chloride, Mercuric Chloride Ammoniated, Mercuric Sodium p-Phenolsulfonate, Mercuric Succinimide, Mercuric Sulfide Red, Mercurophen, Mercurous Acetate, Mercurous Chloride, Mercurous Iodide, Nitromersol, Potassium Tetraiodomercurate (II), Potassium Triiodomercurate(II) Solution Thimerfonate Sodium and Thimerosal;
Nitrofurans such as Furazolidone, 2-(Methoxymethyl)-5-nitrofuran, Nidroxyzone, Nifuroxime, Nifurzide and Nitrofurazone;
Phenols such as Acetomeroctol, Bithionol, Cadmium Salicylate, Carvacrol, Chloroxylenol, Clorophene, Creosot, Cresol(s), p-Cresol Fenticlor, Hexachlorophene, 1-Naphthyl Salicylate, 2-Naphthyl Salicylate, 2,4,6-Tribromo-m-cresol and 3',4',5-Trichlorosalicylanilide;
Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxquinoline Sulfate and Iodochlorhydroxyquin; and
others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol®, Noxytiolin, Ornidazole, β-Propiolactonex α-Terpineol.
68) Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Feripiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trimebutine, N,N-1Trimethyl-3,3-diphenyl-propylamine, Tropenzile, Trospium Chloride and Xenytropium Bromide.

69) Antithrombotic drugs such as Anagrelide, Argatroban, Cilostazol, Daltroban, Defibrotide, Enoxaparin, Fraxiparine®, Indobufen, Lamoparan, Ozagrel, Picotamide, Plafibride, Tedelparin, Ticlopidine and Triflusal.

70) Antitussive drugs such as Alloclamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

71) Antiulcerative drugs such as Aceglutamide Aluminum Complex, ε-Acetamidocaproic Acid Zinc salt, Acetoxolonei, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Omoprostil, γ-Oryzanol, Pifamine, Pirdenzepine, Plaunotol, Ranitidine, Rioprostil, Rosaprostol, Rotraxate, Roxatidine Acetate, Sofalcone, Spizofurone, Sucralfate, Teprenone, Trimoprostil, Trithiozine, Troxipide and Zolimidine.

72) Antiurolithic drugs such as Acetohydroxamic Acid, Allopurinol, Potassium Citrate and Succinimide.

73) Antivenin drugs such as Lyovac® Antivenin.

74) Antiviral drugs, Including:
Purines and pydrimidinones such as Acyclovir, Cytarabine, Dideoxyadenosine, Dideoxycytidine, Dideoxyinosine, Edoxudine, Floxuridine, Ganciclovir, Idoxuridine Inosine Pranobex, MADU, Trifluridine Vidarabine and Zidovudine; and
others such as Acetylleucine Monoethanolamine, Amantadine, Amidinomycin, Cuminaldehyde Thiosemicarbazone, Foscarnet Sodium, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid.

75) Anxiolytic drugs, including:
Arylpiperazines such as Buspirone, Gepirone and Ipsapirone;
Benzodiazepine derivatives such as Alprazolam, Bromazepam, Camazepam, Chlordiazepoxide, Clobazam, Clorazepate, Clotiazepam, Cloxazolam, Diazepam, Ethyl Lofiazepate, Etizolam, Fludiazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepram and Tofisopam;
Carbamates such as Cyclarbamate, Emylcamate, Hydroxyphenamate, Meprobamate, Phenprobamate and Tybamate; and
others such as Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone.

76) Benzodiazepine Antagonists such as Flumazenil.

77) Bronchodilators, including:
Ephedrine derivatives such as Albuterol, Bambuterol, Bitolterol Carbuterol, Clenbuterol, Clorprenaline, Dioxethedrine, Ephedrine Epinephrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbuterol and Tulobuterol;
Quaternary ammonium compounds such as Bevonium Methyl Sulfate, Flutropium Bromide, Ipratropium Bromide and Oxitropium Bromide;
Xanthine derivatives such as Acefylline, Acefylline Piperazine, Ambuphylline, Aminophylline, Bamifylline, Choline Theophyllinate, Doxofylline, Dyphylline, Enprofylline, Etamiphyllin, Etofylline, Guaithylline, Proxyphylline, Theobromine, 1-Theobromineacetic Acid and Theophylline; and
others such as Fenspinide, Medibazine, Methoxyphenanime and Tretoquinol.

78) Calcium channel blockers, including:
Arylalkylamines such as Bepridil, Diltiazem, Fendiline, Gallopanil, Prenylamine, Terodiline and Verapamil;
Dihydropyridine derivatives such as Felodipine, Isradipine, Nicardipine, Nifedipine, Nilvadipine, Nimodipine, Nisoldipine and Nitrendipine;
piperazine derivatives such as Cinnarizine, Flunarizine and Lidoflazine; and
others such as Bencyclane, Etafenone and Perhexiline.

79) Calcium regulators such as Calcifediol, Calcitonin, Calcitriol Clodronic Acid, Dihydrotachysterol, Elcatonin, Etidronic Acid, Ipriflavone, Pamidronic Acid, Parathyroid Hormone and Teriparatide Acetate.

80) Cardiotonics such as Acefylline, Acetyldigititoxins, 2-Amino-4-picoline, Amrinone, Benfurodil Hemisuccinate, Bucladesine, Cerberoside, Camphotamide, Convallatoxin, Cymarin, Denopamine, Deslanoside, Digitalin, Digitalis, Digitoxin, Digoxin Dobutamine, Dopamine Dopexamine, Enoximone, Erythrophleine; Fenalcomine Gitalin, Gitoxin Glycocyamine, Heptaminol, Hydrastinine Ibopamine, Lanatosides Metamivam, Milrinone Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.

81) Chelating agents such as Deferoxamine, Ditiocarb Sodium Edetate Calcium bisodiuml Edetate Disodium, Edetate Sodium, Edetate Trisodium, Penicillamine, Pentetate Calcium Trisodium, Pentetic Acid, Succimer and Trientine.

82) Cholecystokinin antagonists such as Proglumide.

83) Cholelitholytic agents such as Chenodiol, Methyl tert-Butyl Ether, Monooctanoin and Ursodiol.

84) Choleretics such as Alibendol) Anethole Trithion, Azintamide Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol Florantyrone, Hymecromone, Menbutone, 3-(o-Methoxyphenyl)-2-phenylacrylic Acids Metochalcone$_1$ Moquizone, Osalimid, Ox Bile Extract, 4,4'-Oxydi-2-butanol, Piprozolin, Prozapine, 4-Salicyloylmorpholine, Sincalide, Taurocholic Acid, Timonacic, Tocamphyl, Trepibutone and Vanitiolide.

85) Cholinergic agents such as Aceclidine, Acetylcholine Bromide, Acetylcholine Chloride, Aclatonium Napadisilate, Benzpyrinium Bromide, Bethanechol, Chloride, Carbachol, Carpronium Chloride, Demecarium Bromide, Dexpantherol, Diisopropyl Paraoxon$_1$ Echothiophate Iodide. Edrophomium Chloride, Eseridine, Furtrethonium, lsoflurcphate, Methacholine, Chloride, Muscarine, Neostigmine, Oxapropanium, Iodide, Physostigmine and Pyridostigmine Bromide.
86) Cholinesterase inhibitors such as Ambenonium Chloride, Distigmine Bromide and Gaclanthamine.
87) Cholinesterase reactivators such as Obidoxime Chloride and Pralidoxime Chloride.
88) Central nervous system stimulants and agents such as Amineptine, Amphetamine Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate Diethylpropion, N-Ethytlamphetamine, Ethamivan, Etifelmin, Etryptamine, Fencamfamine, Fenethylline, Fenozolone, Flurothyl, Hexacyclonate Sodium, Homocamfin, Mazindol, Mefexamide, Metharphetamine, Methylphenidate, Nikethamide, Pemoline, Pentylenetetrazole, Phendimetrazine, Phenmetrazine, Phentermine, Picrotoxin, Pipradrol, Prolintane and Pyrovalerone.
89) Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, Oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.
90) Dental caries prophylaxis such as Sodium Fluoride.
91) Depigmentors such as Hydroquinine, Hydroquinone and Monobenzone.
92) Diuretics, including:
Organomercurials such as Chlormerodrin, Meraliunde, Mercamphamide, Mercaptomerin Sodium, Mercumallylic Acid, Mercumatilin Sodium, Mercurous Chloride and Mersalyl;
Pteridines such as Furterene and Triamterene;
Purines such as Acefylline, 7-Morpholinomethyltheophylline, Pamabrom, Protheobromine and Theobromine;
Steroids such as Canrenone, Oleandrin and Spironolactone;
Sulfonamide derivatives such as Acetazolamide, Ambuside, Azosemide, Bumetanide, Butazolamide, Chloraminophenamide, Clofenamide, Clopamide, Clorexolone, Diphenylmethane-4,4'-disulfonamide, Disulfamide, Ethoxzolamide, Furosemide, Indapamide, Mefruside, Methazolamide, Piretanide, Quinethazone, Torasemide, Tripamide and Xipamide;
Uracils such as Aminometradine and Amisometradine;
others such as Amanozine, Amiloride, Arbutin, Chlorazanil, Ethacrynic Acid, Etozolin, Hydracarbazine, Isosorbide, Mannitol, Metochalcone, Muzolimine, Perhexiline, Ticrynafen and Urea.
93) Dopamine receptor agonists such as Bromocriptine, Dopexamine, Fenoldopam, Ibopamine, Lisurde, Naxagolide and Pergolide.
94) Ectoparasiticides such as Amitraz, Benzyl Benzoate, Carbaryl, Crotamiton DDT Dixanthogen Isobornyl Thiocyanoacetate-Technical, Lime Sulfurated Solution, Lindane, Malathion, Mercuric Oleate, Mesulphen and Sulphur-Pharmaceutical.
95) Enzymes, including: Digestive enzymes such as α-Amylase (Swine Pancreas), Lipase, Pancrelipase, Pepsin and Rennin;
Mucolytic enzymes such as Lysozyme;
Penicillin inactivating enzymes such as Penicillinase; and
Proteolytic enzymes such as Collagenase, Chymopapain, Chymotrypsins, Papain and Trypsin.
96) Enzyme Inducers (hepatic) such as Flumecinol.
97) Estrogens, Including:
Nonsteroidal estrogens such as Benzestrol, Broparoestrol, Chlorotrianisene, Dienestrol, Diethylstilbestrol, Diethylstilbestrol Dipropibnate, Dimestrol, Fosfestrol, Hexestrol, Methallenestril and Methestrol; and
Steroidal estrogens such as Colpormon, Conjugated Estrogenic Hormones, Equilenin, Equilin, Estradiol Estradiol Benzoate, Estradiol 17β-Cypionate, Estriol, Estrone, Ethinyl Estradiol, Mestranol, Moxestrol, Mytatrienediol, Quinestradiol and Quinestrol.
98) Gastric secretion inhibitbrs-such as Enterogastrone and Octreotide.
99) Glucocorticoids such as 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazoli, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone, Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, Hydrocortisone Phosphate, Hydrocortisone 21-Sodium Succinate, Hydrocortisone Tebutate, Mazipredone, Medrysone, Meprednisone, Methylprednisolone, Mometasone Furoate, Paramethasone, Predaicarbate, Prednisolone, Prednisolone 21-Diethylaminoacetate, Prednisone Sodium Phosphate, Prednisolone, Sodium Succinate, Prednisolone Sodium 21 m-Sulfobenzoate, Prednisolone 21-Stearoylglycolate, Prednisolone Tebutate, Prednisolone 21-Trimethylacetate, Preidnisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide
100) Gonad-Stimulating principles such as Buserelin, Clomiphene, Cyclofenil, Epimestrol, FSH, HCG and LH-RH.
101) Gonadotropic hormones such as LH and PMSG.
102) Growth hormone inhibitors such as Octreotide and Somatostatin.
103) Growth hormone releasing factors such as Semorelin.
104) Growth stimulants such as Somatotropin.
105) Hemolytic agents such as Phenylhydrazine and Phenylhydrazine Hydrochloride.
106) Heparin antagonists such as Hexadimethrine Bromide and Protamines.
107) Hepatoprotectants such as S-Adenosylmethionine, Betaine, Catechin, Citiolone, Malotilate, Orazamide, Phosphorylcholine, Protoporphyrin IX, Silymarin-Group, Thioctic Acid and Tiopronin.
108) mimunomodulators such as Amiprilose, Bucillamine, Ditiocarb Sodium, Inosine Pranobex, Interferon-γinterleukin-2, Lentinan, Muroctasin, Platonin, Procodazole, Tetramisole, Thymomodulin, Thymopentin and Ubenimex.
109) Immunosuppressants such as Azathioprine, Cyclosporins and Mizoribine.
110) Ion exchange resins such as Carbacrylic Resins, Cholestyramine Resin, Colestipol, Polidexide, Resodec and Sodium Polystyrene Sulfonate
111) Lactation stimulating hormone such as Prolactin.
112) LH-RH agonists such as Buserelin, Goserelin, Leuprolide, Nafarelin and Triptorelin.

113) Lipotropic agents such as N-Acetylmethionine, Choline Chloride, Choline Dehydrocholate Choline Dihydrogen Citrate Inositol, Lecithin and Methionine.
114) Lupus erythematosus suppressants such as Bismuth Sodium Triglycollamate, Bismuth Subsaticylate, Chloroquine and Hydroxychloroquine.
115) Mineralcorticoids such as Aldosterone, Deoxycorticosterone, Deoxycorticosterone Acetate and Fludrocortisone.
116) Miotic drugs such as Carbachol, Physostigmine, Pilocarpine and Pilocarpus.
117) Monoamine oxidase inhibitors such as Deprenyl, Iproclozide, Iproniazid, Isocarboxazid, Moclobemide, Octamoxin, Pargyline Pheneizine, Phenoxypropazine, Pivalylbenzhydrazine, Prodipine, Toloxatone and Tranylcypromine.
118) Mucolytic agents such as Acetylcysteine Bromhexine Carbocysteine, Domiodol, Letosteine, Lysozyme, Mecysteine Hydrochloride, Mesna, Sobrerol, Stepronin, Tiopronin and Tyloxapol.
119) Muscle relaxants (skeletal) such as Afloqualone, Alcuronium, Atracurium Besylate, Baclofen, Benzoctamine, Benzoquinonium Chloride, C-Calebassine, Carisoprodol Chlormezanone Chlorphenesin Carbamate, Chlorproethazine, Chlorzoxazone, Curare, Cyclarbamate. Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Laudexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam Thiocolchicoside, Tizanidine, Tolperisone Tubocurarine Chloride Vecuronium Bromide and Zoxazolamine.
120) Narcotic antagonists such as Amiphenazole, Cyclazocine, Levallorphan, Nadide, Nalmefenef Nalorphine, Nalorphine Dinicotinate, Naloxone and Naltrexone.
121) Neuroprotective agents such as Dizocilpine.
122) Nootropic agents such as Aceglutamide, Acetylcarnitine, Aniracetam, Bifemelane, Exifone, Fipexide, Idebehone, Indeloxazine Hydrochloride Nizofenone, Oxiracetam, Piracetam, Propentofylline, Pyritinol and Tacrine.
123) Ophthalmic agents such as 15-ketoprostaglandins.
124) Ovarian hormone such as Relaxin.
125) Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_2\alpha$ and Sparteine.
126) Pepsin inhibitors such as Sodium Amylosulfate.
127) Peristaltic stimulants such as Cisapride:
128) Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Flurogestone Acetate, Gestodene, Gestonorone Caproate, Haloprogesterone 17-Hydroxy-16-methylene-progesterone, 17-Hydroxyprogesterone, 17α-Hydroxyprogesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone.
129) Prolactin inhibitors such as Metergoline.
130) Prostaglandins and prostaglandin analogs such as Arbaprostil, Carboprost, Enprostil, Gemeprost, Limaprost, Misoprostol Ornoprostil, Prostacyclin, Prostaglandin $E_1$, Prostaglandin $E_2$, Prostaglandin $F_2\alpha$, Rioprostil, Rosaprostol, Sulprostone and Trimoprostil.
131) Protease Inhibitors such as Aprotinin, Camostat, Gabexate and Nafamostat.
132) Respiratory stimulants such as Almitrine, Bemegride, Carbon Dioxides, Cropropamide, Crotethamide, Dimefline, Dimorpholamine, Doxapram, Ethamivam, Fominoben, Lobeline, Mepixanox, Metamivam, Nikethamide, Picrotoxin, Pimeclone, Pyridofylline, Sodium Succinate and Tacrine.
133) Sclerosing agents such as Ethanolamine Ethylamine 2-Hexyldecanoic Acid, Polidocanol, Quinine Bisulfate, Quinine Urea Hydrochloride, Sodium Ricinoleate, Sodium Tetradecyl Sulfate and Tribenroside.
134) Sedatives and hypnotics, including:
Acyclic ureides such as Acecarbromal, Apronalide, Bomisovalum, Capuride, Carbrormal and Ectylurea;
Alcohols such as Chlorhexadol, Ethchlorvynol, Meparfynol, 4-Methyl-5-thiazoleethanol, tert-Pentyl Alcohol and 2,2, 2-Trichloroethanol;
Amides such as Butoctamide, Diethylbromoacetamide, Ibrotamide, Isovaleryl Diethylamide, Niaprazine, Tricetamide, Trimetozine, Zolpidem and Zopiclone;
Barbituric acid derivatives such as Allobarbital, Amobarbital, Aprobarbital, Barbital, Brallobarbital, Butabarbital Sodium, Butalbitalf, Butallylonal, Butethal, Carbubarb, Cyclobarbital, Cyclopentobarbital, Enallylpropymal, 5-Ehtyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbtal Sodium and Vinylbital;
Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;
Bromides such as Ammonium, Bromide, Calcium Bromide Calcium Bromolactobionate, Lithium Bromide, Magnesium Bromide, Potassium Bromide and Sodium Bromide;
Carbamates such as Amyl Carbamate-Tertiary, Ethinamate, Hexapropymate, Meparfynol Carbamate, Novonal and Trichlorourethan;
Chloral derivatives such as Carbocloral, Chloral Betaine, Chloral Formamides, Chloral Hydrate, Chloralatipyrine, Dichoralphenazone, Pentaerythritol Chloral and Triclofos;
Pipendinediones such as Glutethimide; Methyprylon, Piperidione, Pyrithyldione, Taglutimide and Thalidomide;
Quinazolone derivatives such as Etaqualone, Mecloqualone and Methaqualone; and
others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chloralose Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone Sodium Oxybate, Sulfonethylmethane and Sulfonmethane.

25

135) Thrombolytic agents such as APSAC, Plasmin, Pro-Urokinase, Streptokinase, Tissue Plasminogen Activator and Urokinase.
136) Thyrotropic hormones such as TRH and TSH.
137) Uricosurics such as Benzbromarone, Ethebenecide, Orotic Acid, Oxycinchophen, Probenecid, Sulfinpyrazone, Ticrynafen and Zoxazolamine.
138) Vasodilators (cerebral) such as Bencyclane, Cinnarizine, Citicoline, Cyclandelate, Ciclonicate, Diisopropylamine Dichloroacetate, Eburnamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.
139) Vasodilators (coronary) such as Amotriphene, Bendazol, Benfurodil Hemisuccinate, Benziodarone, Chloracizine, Chromonar Clobenfurol, Clonitrate, Dilazep, Dipyridamole, Droprenilamine, Efloxate, Erythritol, Erythrityl Tetranitrate, Etafenone, Fendiline, Floredil, Ganglefene), Hexestrol Bis(β-diethylaminoethyl ether), Hexobendine, Itramin Tosylate, Khellin, Lidoflazine, Mannitol Hexanitrate, Medibazine Nicorandil, Nitroglycerin, Pentaerythritol Tetranitrate, Pentrinitrol, Perhexiline, Pimethylline, Prenylamine, Propatyl Nitrate, Pyrdofylline, Trapidil, Tricromyl, Trimetazidine, Trolnitrate Phosphate and Visnadine.
140) Vasodilators (peripheral) such as Aluminum Nicotinate, Bamethan Bencyclane, Betahistine, Bradykinin, Brovincamined, Bufoniode, Buflomedil Butalamine, Cetiedit, Cicionicate, Cinepazide, Cinnarizine, Cyclandelate, Diisopropylamine Dichloracetate, Eledoisin, Fenoxedil, Flunarizine, Hepronicate, Ifenprodil, Inositol Niacinate, Isoxsuprine, Kallidin, Kallikrein, Moxisylyte, Nafronytl, Nicametate, Nicergoline, Nicofuranose, Nicotinyl Alcohol, Nylidein, Pentifylline, Pentoxifylline, Piribedil, Prostaglandin $E_1$. Suloctidil and Xanthinol Niacinate.
141) Vasoprotectants such as Benzarone, Bioflavonoids, Chromocarb, Clobenoside, Diosmin, Dobesilate Calcium, Escin, Folescutol, Leucocvanidin, Metescufylline, Quercetin, Rutin and Troxerutin.
142) Vitamins, vitamin sources and vitamin extracts such as Vitamins A, B, C, D, E and K and derivatives thereof, Calciferols, Glycyrrhiza, and Mecobalamin.
143) Vulnerary agents such as Acetylcysteine, Allantoin, Asiaticoside, Cadexomer Iodine, Chitin, Dextranomer and Oxaceprol.

The use referred to herein increases percutaneous absorption of drugs by over 5 times their normal capacity.

Finally, the invention also regards the compounds belonging to the Perfluoropolyester class of formula I

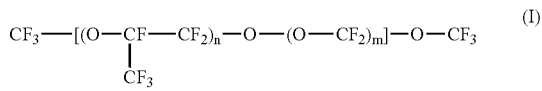

with n and m>18 and <46 and with molecular weights between ~600 and ~8000, especially those with n and m>24 and <36 with molecular weights between 1000 and 4000, obtained by polymerization of hexafluoropropene

26

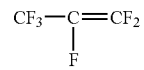

with UV activated oxygen.

The invention claimed is:

1. A pharmaceutical composition comprising, in addition to one or more pharmacologically active ingredient, wherein the active ingredient is Troxerutine, Nimesulide, or a non-steroidal anti-inflammatory drug, wherein said non-steroidal anti-inflammatory drug is Ketoprofen, Diclofenac Sodium, Ibuprofen, Etodolic Acid, Piroxicam, or a combination thereof, between 0.01 percent and 60 percent by weight of a compound of formula I

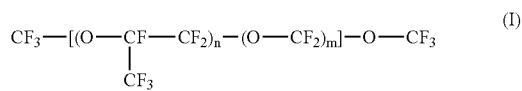

with n and m>18 and <46 and with a molecular weight between about 600 and about 18,000, in combination with 0.01% to 20% by weight of phosphatidylcholine, for enhancement of active-ingredient absorption.

2. A pharmaceutical composition according to claim 1 with 0.1 percent to 30 per cent by weight of the compound of formula I with n and m>24 and <36 and with the molecular weight between 1,000 and 4,000.

3. A pharmaceutical composition according to claim 1, wherein the composition is in a form selected from the group consisting of creams, emulsions, ointments, lotions, foams, gels, aspersion powders, and transdermal formulations.

4. A method for enhancing absorption of a pharmacologically active ingredient, wherein the method comprises topically applying the pharmaceutical composition claimed in claim 1 to a patient in need thereof wherein the active ingredient is absorbed through derma, cutis, mucosa, rectum, vagina, or urethra.

5. A pharmaceutical composition according to claim 2, wherein the composition is in a form selected from the group consisting of creams, emulsions, ointments, lotions, foams, gels, aspersion powders, and transdermal formulations.

6. The composition according to claim 1, wherein trans-absorption of the active ingredient is increased by up to more than five times its normal value.

7. The composition according to claim 2, wherein trans-absorption of the active ingredient is increased by up to more than five times its normal value.

8. A method for enhancing absorption of a pharmacologically active ingredient, wherein the method comprises topically applying the pharmaceutical composition claimed in claim 2 to a patient in need thereof, wherein the active ingredient is absorbed through derma, cutis, mucosa, rectum, vagina, or urethra.

9. A pharmaceutical composition as claimed in claim 1, wherein trans-absorption of the active ingredient is increased by up to more than ten times its normal value.

10. A pharmaceutical composition as claimed in claim 1, wherein trans-absorption of the active ingredient is increased by up to more than 20 times its normal value.

11. A method as claimed in claim 4, wherein trans-absorption of the active ingredient is increased by up to more than ten times its normal value.

12. A method as claimed in claim 4, wherein trans-absorption of the active ingredient is increased by up to more than 20 times its normal value.

13. A pharmaceutical composition as claimed in claim 1, wherein the active ingredient is troxerutine.

14. A method as claimed in claim 4, wherein the active ingredient is troxerutine.

15. A pharmaceutical composition consisting essentially of
   (1) one or more pharmacologically active ingredient, wherein the active ingredient is Troxerutine, Nimesulide, or a nonsteroidal anti-inflammatory drug, wherein said non-steroidal anti-inflammatory drug is Ketoprofen, Diclofenac Sodium, Ibuprofen, Etodolic Acid, Piroxicam, or a combination thereof;
   (2) between about 0.01 percent and about 60 percent by weight of a compound of formula I

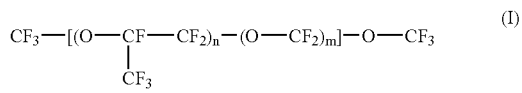

wherein n and m are each greater than 18 and are each less than 46 and wherein the compound of the formula I has a molecular weight between about 600 and about 8,000;
   (3) phosphatidylcholine;
   (4) optionally tocopherol acetate;
   (5) optionally polyacrylamide, $C_{13}$–$C_{14}$ isoparaffin, and laureth-7;
   (6) optionally methyl-p-hydroxybenzoate;
   (7) optionally propyl-p-hydroxybenzoate;
   (8) optionally phenoxyethanol;
   (9) optionally nor-chenodeoxycolic acid;
   (10) optionally transcutol; and
   (11) optionally water.

16. A pharmaceutical composition consisting essentially of:
   (1) one or more pharmacologically active ingredient, wherein the active ingredient is Troxerutine, Nimesulide, or a non steroidal anti-inflammatory drug, wherein said non-steroidal anti-inflammatory drug is Ketoprofen, Diclofenac Sodium, Ibuprofen, Etodolic Acid, Piroxicam, or a combination thereof;
   (2) between about 0.01 percent and about 60 percent by weight of a compound of formula I

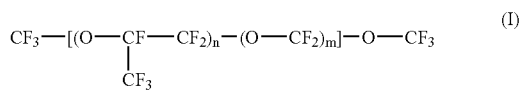

wherein n and m are each greater than 18 and are each less than 46 and wherein the compound of the formula I has a molecular weight between about 600 and about 8,000;
   (3) phosphatidylcholine;
   (4) optionally tocopherol acetate;
   (5) optionally polyacrylamide, $C_{13}$–$C_{14}$ isoparaffin, and laureth-7;
   (6) optionally methyl-p-hydroxybenzoate;
   (7) optionally propyl-p-hydroxybenzoate;
   (8) optionally phenoxyethanol;
   (9) optionally nor-chenodeoxycolic acid;
   (10) optionally transcutol;
   (11) optionally lactic acid;
   (12) optionally ethyl alcohol; and
   (13) optionally water.

17. A pharmaceutical composition as claimed in claim 15, wherein the active ingredient is troxerutine.

18. A pharmaceutical composition according to claim 15, wherein the phosphatidlycholine constitutes 0.01 percent to 10 percent by weight of the pharmaceutical composition, and wherein the compound of the formula I has a molecular weight between 1,000 and about 4,000 with n and m each greater than 24 and each less than 36.

19. A pharmaceutical composition according to claim 17, wherein the phosphatidlycholine constitutes 0.01 per cent to 10 percent by weight of the pharmaceutical composition, and wherein the compound of the formula I has a molecular weight between 1,000 and about 4,000 with n and m each greater than 24 and each less than 36.

20. A pharmaceutical composition as claimed in claim 16, wherein the active ingredient is troxerutine.

21. A pharmaceutical composition according to claim 16, wherein the phosphatidlycholine constitutes 0.01 percent to 10 percent by weight of the pharmaceutical composition, and wherein the compound of the formula I has a molecular weight between 1,000 and about 4,000 with n and m each greater than 24 and each less than 36.

22. A pharmaceutical composition according to claim 20, wherein the phosphatidlycholine constitutes 0.01 percent to 10 percent by weight of the pharmaceutical composition, and wherein the compound of the formula I has a molecular weight between 1,000 and about 4,000 with n and m each greater than 24 and each less than 36.

23. The method according to claim 4, wherein the active ingredient is Troxerutine, Nimesulide, Ketopropfen, Etodolic Acid, or a combination thereof.

24. The pharmaceutical composition as claimed in claim 15, wherein the active ingredient is Troxerutine, Nimesulide, Ketopropfen, Etodolic Acid, or a combination thereof.

25. The pharmaceutical composition as claimed in claim 15, wherein the active ingredient is Troxerutine, Nimesulide, Ketopropfen, Etodolic Acid, or a combination thereof.

26. The pharmaceutical composition as claimed in claim 16, wherein the active ingredient is Troxerutine, Nimesulide, Ketopropfen, Etodolic Acid, or a combination thereof.

27. The pharmaceutical composition as claimed in claim 1, wherein phosphatidylcholine is 0.01% to 10% by weight of the pharmaceutical composition.

28. The pharmaceutical composition as claimed in claim 15, wherein the composition consists essentially of the one or more active ingredient, wherein the active ingredient is Troxerutine, Nimesulide, or a non-steroidal anti-inflammatory drug, wherein said nonsteroidal anti-inflammatory drug is Ketoprofen, Diclofenac Sodium, Ibuprofen, Etodolic Acid, Piroxicam, or a combination thereof, the compound formula I, the phosphatidylcholine, and optionally the water.

29. A method according to claim 4, wherein trans-absorption of the active ingredient is increased by up to more than five times its normal value.

* * * * *